US008206336B2

(12) United States Patent \
Shantha

(10) Patent No.: US 8,206,336 B2 \
(45) Date of Patent: *Jun. 26, 2012

(54) METHODS FOR REDUCING PAIN USING A TRANSDERMAL LOCAL ANESTHETIC PATCH WITH INJECTION PORT IN COMBINATION WITH AN ELECTROMOTIVE FORCE

(76) Inventor: Totada R. Shantha, McDonough, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/022,048

(22) Filed: Feb. 7, 2011

(65) Prior Publication Data

US 2011/0166498 A1 Jul. 7, 2011

Related U.S. Application Data

(63) Continuation-in-part of application No. 12/424,799, filed on Apr. 16, 2009, now Pat. No. 7,883,488, which is a continuation-in-part of application No. 12/338,381, filed on Dec. 18, 2008, now Pat. No. 7,883,487.

(60) Provisional application No. 61/132,134, filed on Jun. 16, 2008.

(51) Int. Cl.
*A61B 17/20* (2006.01)

(52) U.S. Cl. ...................................... 604/22

(58) Field of Classification Search ............... 604/890.1, 604/20, 22, 65, 66, 67, 116, 19, 112, 289; 424/449; 514/447

See application file for complete search history.

(56) References Cited

U.S. PATENT DOCUMENTS

| 4,460,368 | A | * | 7/1984 | Allison et al. | 424/449 |
| 5,415,866 | A | * | 5/1995 | Zook | 424/448 |
| 7,981,071 | B2 | * | 7/2011 | Goldberg | 604/22 |
| 2004/0267299 | A1 | * | 12/2004 | Kuriger | 606/181 |
| 2008/0086063 | A1 | | 4/2008 | Baxter et al. | |
| 2008/0086187 | A1 | | 4/2008 | Baxter et al. | |

OTHER PUBLICATIONS

Anthony Eidelman, MD, et al; Topical Anesthetics for Dermal Instrumentation: A Systematic Review of Randomized, Controlled Trials; vol. 46, No. 4: Oct. 2005: Annals of Emergency Medicine; 9 pages.
Bruce M. Becker, MD, et al; Ultrasound with Topical Anesthetic Rapidly Decreases Pain of Intravenous Cannulation; vol. 12, No. 4; Apr. 2005; ACAD Emerg MED; 7 pages.
Nathaniel P. Katz, MD, et al; Rapid Onset of Cutaneous Anesthesia With EMLA Cream After Pretreatment with a New Ultrasound-Emitting Device; 2004; International Anesthesia Research Society; 6 pages. Yi-Hui Wu, et al; Thermal Effect of Sonophoresis for Accelerating the Analgesic Effect of Local Anesthetics on Rat Tail Nerve; 2008; 30th Annual International IEEE EMBS Conference; 4 pages.
J. Sawyer, et al; Heated lidocaine/tetracain patch (Synera, Rapydan) compared with lidocaine/prilocaine cream (EMLA) for topical anaesthesia before vascular access; The Board of Management and Trustees of the British Journal of Anaesthesia 2009; 6 pages.

\* cited by examiner

*Primary Examiner* — Nicholas Lucchesi \
*Assistant Examiner* — Brooke Matney \
(74) *Attorney, Agent, or Firm* — Gardner Groff Greenwald & Villanueva P.C.

(57) ABSTRACT

Described herein are transdermal delivery devices composed of at least one resealable injection port and at least one local anesthetic reservoir. The device effectively delivers anesthetic to the skin of the subject prior to puncturing the skin by syringes, needle sticks, or other instruments intended to be inserted into the skin. In addition, the transdermal delivery device may include a single use patch that does not include a local anesthetic refill port. The devices are used in combination with an electromotive force in order to enhance pain reduction when a subject is injected with a needle. Devices for imparting an electromotive force to a subject are also described herein.

23 Claims, 11 Drawing Sheets

METHODS FOR REDUCING PAIN USING A TRANSDERMAL LOCAL ANESTHETIC PATCH WITH INJECTION PORT IN COMBINATION WITH AN ELECTROMOTIVE FORCE

CROSS-REFERENCE TO RELATED APPLICATION

This application is a continuation-in-part of U.S. non-provisional application Ser. No. 12/424,799 filed on Apr. 16, 2009, which claims priority upon continuation-in-part U.S. non-provisional application Ser. No. 12/338,381 filed on Dec. 18, 2008, which claims priority upon U.S. provisional application No. 61/132,134, filed Jun. 16, 2008. The entireties of these applications are incorporated by this reference.

BACKGROUND

An overarching fear of needles and needle sticks exists throughout the world. This fear knows no bounds of age, sex, or race. For many, this phobia makes visits to the doctor and dentist intolerable and often times a last resort. This ultimately results in missed doctor's and dentist's visits and inadequate healthcare treatment of various illnesses, diseases and for routine vaccinations.

For people with this phobia coupled with chronic diseases such as, for example, insulin dependent diabetes, treatment is a daunting task. These patients face the daily task of sticking their finger with a lancet to draw blood to test blood sugar. For a noncompliant patient, this complicates diagnosis and treatment of the condition, and even for the most compliant patient, the task of repeatedly sticking their finger with a lancet is extremely painful. In addition, for a compliant patient each day the patient must administer medication or insulin via an injection. After administering their medication, proper sterile techniques require one to sterilize the injection site and place a bandage where the injection took place. This process is tedious and mundane. Many people fail to follow proper sterile techniques, and as a result, the injection site may become infected. For those people who do follow this protocol, the skin is often damaged due to the constant application and removal of bandage adhesives. Thus, it would be desirable for the subject to have a patch containing a local anesthetic to numb the injection site, an antiseptic or antimicrobial agent to prevent injection site infection, and either a single use or multi-use injection port to allow for a pain free injection for as many days as needed.

SUMMARY

Described herein are transdermal delivery devices composed of at least one resealable injection port and at least one local anesthetic reservoir. The device effectively delivers anesthetic to the skin of the subject prior to puncturing the skin by syringes, needle sticks, or other instruments intended to be inserted into the skin. In addition, the transdermal delivery device may include a single use patch that does not include a local anesthetic refill port. The devices are used in combination with an electromotive force in order to enhance pain reduction when a subject is injected with a needle. Devices for imparting an electromotive force to a subject are also described herein.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
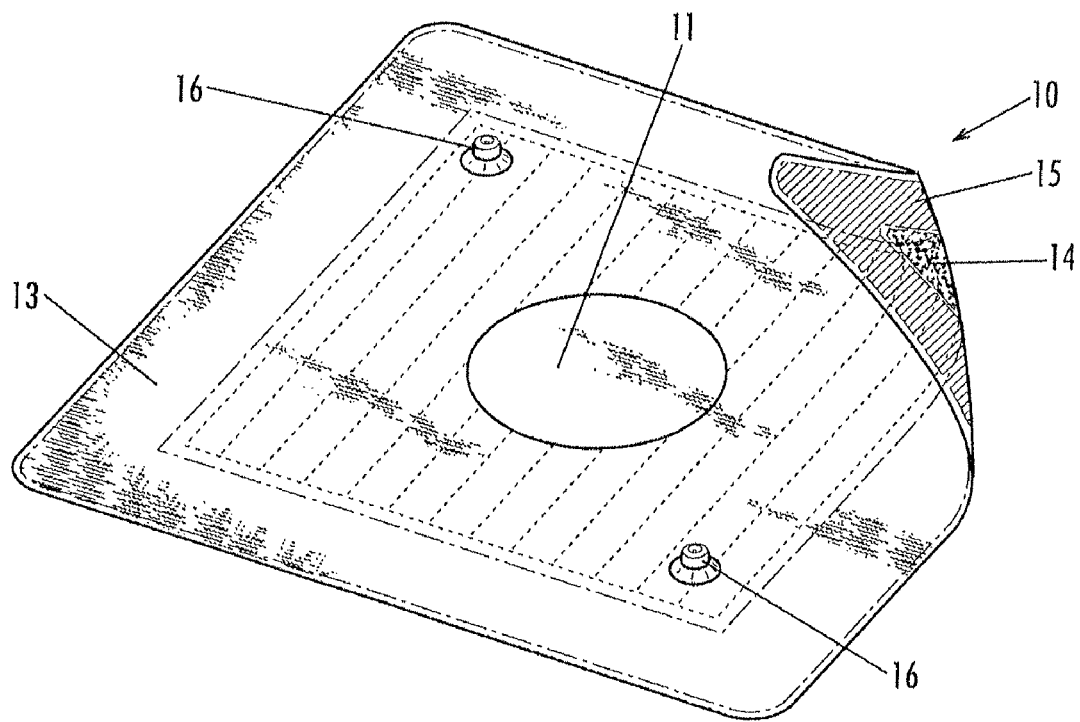
FIG. 1 shows the top view of a transdermal delivery device with a single injection port, two resealable refill ports, and an anesthetic reservoir.

Before the present compounds, compositions, and/or methods are disclosed and described, it is to be understood that the aspects described below are not limited to specific compositions, compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a local anesthetic" includes mixtures of two or more such anesthetics, and the like.

The term "subject" as used herein is any mammal that is susceptible to pain due to an injection of the skin. Examples of mammal include humans, domestic animals (e.g., dogs, cats, horses), livestock (e.g., cows, pigs, sheep), and wild animals.

The injection needle or Hypodermic needles as used herein includes, but is not limited to, all different types of sharp pointed needles, pins, probes, sharp instruments and the like that can be used to inject therapeutic agents; remove, or introduce fluid medications; lance, incise, evacuate tissues of the body, and the like to a patient, as well as to conduct tests such as but not limited to allergy tests to a patient and inject daily hormones such as Insulin in diabetics and other daily, biweekly, thrice weekly injections for health maintenance or as therapeutic agents to treat diseases.

The term "Vibration, vibrational, vibromatic, sonovibramtic, analgesia" as used herein includes, but is not limited to, the use or application of vibration and sound (including ultrasonic from the digital vibration device (DVD) to a patient to induce an analgesic or anesthetic effects of the selected area including the digits for introduction of needle or lancet through the pain sensitive dermis or mucous membrane.

"Optional" or "optionally" means that the subsequently described event or circumstance can or cannot occur, and that the description includes instances where the event or circumstance occurs and instances where it does not. For example, the phrase "optionally a skin permeability enhancer" means that the therapeutic agent may or may not be included.

Effective therapeutic amount refers to the amount of a compound of the present invention that offers therapeutic activity after administration to humans or animals without adverse effects. The therapeutic amount of local anesthetic compounds is referred to as concentration of the active compound and the volume administered.

Described herein are the use of transdermal delivery devices that deliver a local anesthetic to an injection or lancing site in combination with an electromotive force in order to prevent or reduce pain associated with the injection of needles in the skin. The term "injection site" is the location on the subject's skin that is going to be punctured by a medical device including but not The resealable injection port is generally composed of a polymeric, non-allergenic, non-reacting, inert material that permits a medical device such as a syringe or needle to readily pass through the material. During injection, the polymeric material forms a seal around the medical device. Upon removal of the medical device, the polymeric material substantially if not completely closes the hole produced by the medical device. Thus, the resealable injection port can maintain a sterile environment during injection and post-injection. The polymeric material used to make the resealable injection port can be composed of a variety of different materials such as, for example, silicon, non-allergic rubberized material, or other medically safe synthetic or semi-synthetic plastics. The number of injection ports can vary, as will be demonstrated below.

The delivery device also contains one or more local anesthetic reservoirs for holding the local anesthetic. The local anesthetic is generally positioned near the resealable injection port so that the skin at or near the injection site is exposed to the anesthetic and block the nerves of the skin, for a painless entry of a needle or lancet. The local anesthetic can be any topical anesthetic known in the art. In one aspect, the local anesthetic includes ester based or an amide based local anesthetics or any combination thereof. Examples of amide based local anesthetics include, but are not limited to, articaine, bupicaine, dibucaine, lidocaine, mepivacaine, prilocaine, and ropivacaine. Examples of ester based local anesthetics include, but are not limited to, benzocaine, chloroprocaine, proparacaine, and tetracaine. In one aspect, the local anesthetic is a combination of both lidocaine and prilocaine. The lidocaine and prilocaine are present at least in a 2:1 ratio by weight, a 1:1 ratio by weight, or any combination thereof. In other aspects, lidocaine and prilocaine may be present in the amount of 3:1, 4:1, 5:1, 6:1, 7:1, 8:1, 9:1, 10:1, 11:1, 12:1, 13:1, 14:1, 15:1. In addition, any of the local anesthetics mentioned above can be used in combination and are present at least in a 2:1, 3:1, 4:1, 5:1, 6:1, 7:1, 8:1, 9:1, 10:1, 11:1, 12:1, 13:1, 14:1, or 15:1 ratio by weight. Even up to 2:98, 5:95, 10:90, 25:75, 35:65, 50:50 amount respectively. The anesthetic can be mixed with carriers such as lipophilic vehicles in order to enhance the absorption of the anesthetic by the skin. The local anesthetic may be fast-acting or short-acting. For example, one may feel a "numbing" sensation within a matter of minutes. However, this numbing sensation may only last a matter of minutes or hours. In another aspect, the local anesthetic may be long acting. In this aspect, one may feel a "numbing" sensation rather quickly (i.e. in a matter of minutes), and this sensation may last up to at least 18 hours. The selection and amount of the local anesthetic can vary depending upon the size of the delivery device as well as the number and position of resealable injection ports present in the device and how long the patch will be used. The shape and size of the transdermal delivery device can vary depending upon the application, which is demonstrated in the figures. In certain aspects, the shape of the device is a circle, a square, a rectangle, an oval, an oblong shape, a triangle, a star, or a square depending upon where on the subject the device is applied. In general, the device has an adhesive that permits the attachment of the device to the skin of the subject. For example, the transdermal delivery device may be placed onto a finger (like a band aid), the abdomen, thigh, calf, arm, shoulder, or any other regions of exposed skin on the subject. Adhesives typically used in bandages and the like can be used herein.

The devices described herein can contain one or more optional therapeutic agents. The location of the optional therapeutic agents in the device can vary depending upon the design of the device. In one aspect, the optional therapeutic agent can be an antiseptic agent, a therapeutic pharmacological, a biologic, a nutriceutical, hormones, antibiotics, nicotine, antifungal agents, antiviral agents, or any pain relieving agent not excluding narcotics. By preventing bacterial, viral, and fungal growth, antiseptic agents maintain sterility either before, during, or post injection. In one aspect, the antiseptic agent can be an alcohol including, but not limited to, ethanol, propanol, isopropanol, or any combination thereof; quaternary ammonium compounds including, but not limited to, benzalkonium chloride, cetyl trimethylammonium bromide, cetylpyridinium chloride, benzethonium chloride, or any combination thereof; boric acid; chlorhexidine gluconate, hydrogen peroxide, iodine, mercurochrome, octenidine dihydrochloride, sodium chloride, sodium hypochlorite, colloidal silver, silver nitrate, mupirocin, erythromycin, clindamycin, gentamicin, polymyxin, bacitracin, silver, sulfadiazine, or any combination thereof.

In other aspects, the optional therapeutic agent is a vasoconstrictor. Vasoconstriction is the narrowing of blood vessels resulting from the contraction of the muscular wall of the vessels. When blood vessels constrict, the flow of blood is restricted or slowed. Without wishing to be bound by theory, a vasoconstrictor would increase the time a local anesthetic resided at one location. The vasoconstrictor may prevent blood flow washout or dissipation of the local anesthetic. In addition, a vasoconstrictor may limit the amount of bleeding associated with a needle or lancet stick. Such vasoconstrictors may include phenylephrine, ephedrine sulfate, epinephrine, naphazoline, neosynephrine, vasoxyl, oxymetazoline, or any combination thereof.

In another aspect, the optional therapeutic agent is a skin permeability enhancer. The skin is a rigid, almost impermeable layer. This impermeability is attributed to the nature of one very thin top surface layer called the stratum corneum. This impermeability creates problems for the transdermal delivery of agents which include local anesthetics. Examples of skin permeability enhancers include but are not limited to dimethyl sulfoxide (DMSO), lecithin, decyl methyl sulfoxide, dodecyl dimethyl phosphine oxide, octyl methyl sulfoxide, nonyl methyl sulfoxide, undecyl methyl sulfoxide, lauryl alcohol, diisopropyl sebacate, oleyl alcohol, diethyl sebacate, dioctyl sebacate, dioctyl azelate, hexyl laurate, ethyl caprate, butyl stearate, dibutyl sebacate, dioctyl adipate, propylene glycol dipelargonate, ethyl laurate, butyl laurate, ethyl myristate, butyl myristate, isopropyl palmitate, isopropyl isostearate, 2-ethylhexyl pelargonate, butyl benzoate, benzyl benzoate, benzyl salicylate, dibutyl phthalate, nicotinates, fatty acids, fatty alcohols, or any combination thereof. In one aspect, the skin permeability enhancer is at least greater than 1% weight per volume, weight per weight, or mole percent. In another aspect, the skin permeability enhancer may be at least greater than 1.5%, 2.0%, 2.5%, 3.0%, 3.5%, 4.0%, 4.5% up to 50% weight per volume, weight per weight, or mole percent. In one aspect, the skin permeability enhancer is dimethyl sulfoxide. In this aspect, the amount of dimethyl sulfoxide may range from 2% to 10%, 2% to 9.5%, 3% to 8%, 3% to 7%, or 4% to 6% weight per volume, weight per weight, by mole percent or any effective therapeutic amount relative to the local anesthetic.

In other aspects, anti-inflammatories and anti-dolorosa can be present in the device to reduce inflammation. This class of drugs functions to block various inflammatory pathways. For example, non-steroidal anti-inflammatory drugs (NSAIDs) alleviate pain and inflammation by counteracting cyclooxygenase and preventing the synthesis of prostaglandins. In one aspect, NSAIDs may be incorporated in the replaceable button or the semi-permeable reservoir of the transdermal delivery device. These NSAIDs may include celecoxib, meloxicam, nabumetone, piroxicam, naproxen, oxaprozin, rofecoxib, sulindac, ketoprofen, valdecoxid, anti-tumor necrosis factors, anti-cytokines, anti-inflammatory pain causing bradykinins or any combination thereof.

In another aspect, antihistamines and steroids can be used to prevent any allergic reaction or irritation caused by the anesthetic or other therapeutic agents when the device is used for prolonged periods of time.

Figure 2:
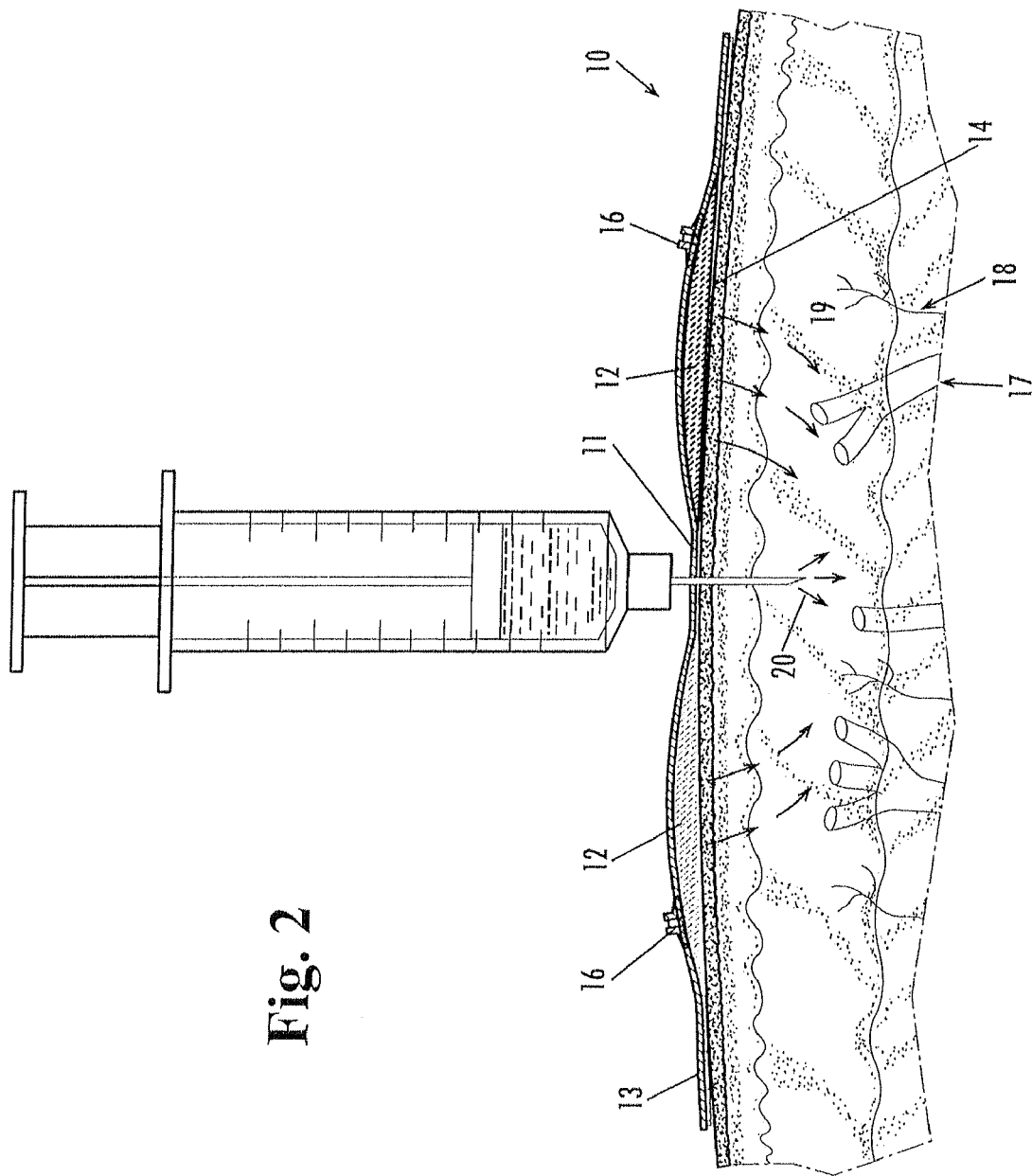
FIG. 2 shows the cross-sectional view of a transdermal delivery device with a single injection port, two resealable refill ports, and an anesthetic reservoir.

FIGS. 1-6 provide numerous designs of the devices described herein. Referring to FIGS. 1 and 2, the transdermal delivery device 10 is a patch having a resealable injection port 11 and a reservoir 12 that contains the local anesthetic or any other pharmaceutically acceptable preparation. On the topside of the device 10, an impermeable substrate 13 surrounds the injection port 11 and prevents the local anesthetic from leaching out of the reservoir. On the underside of the device 10, which is the side that is applied to the surface of the skin, an opposing permeable layer 14 is present and positioned under the reservoir 12. The permeable layer permits the diffusion of the local anesthetic from the reservoir to the skin surface. The permeable layer 14 is surrounded by an impermeable material 15, which prevents the local anesthetic from leaching to the sides of the device 10. An adhesive can be applied to the impermeable material 15, which helps adhere the device to the subject's skin. Semipermeable and permeable membranes may include, but are not limited to, materials made from regenerated cellulose, regenerated cellophane, cellulose ester membranes, charge mosaic membranes, bipolar membranes, amphoteric exchange membranes, anion exchange membranes, dialysis tubing, ethylene-vinyl acetate (EVA) copolymer membranes (e.g. 1-20% vinyl acetate), polyvinylalcohol (PVA) gels, or silicon films.

The device as shown in FIGS. 1 and 2 also permits refilling of the reservoir 12 with local anesthetic or other therapeutic pharmacological agents, biologics, and nutriceuticals once the anesthetic has substantially or completely diffused from the reservoir. Two resealable refill ports 16 are present in the device 10. The number and design of the ports can vary. For example, with smaller devices, the refill port can be composed of a polymeric material such as that used in the injection port, which permits the injection of additional anesthetic into the reservoir without a refill port. The selection of the polymeric material will depend upon the volume of the reservoir in the device and if present, the dimensions of the refill port. If larger devices are contemplated, the refill port can be accessed by a screw top. Thus, the delivery devices depicted in FIGS. 1-3 can be refilled and reused multiple times.

FIG. 2 further depicts inserting a hypodermic needle into the injection port and injecting a bioactive agent 20 within the dermal or subdermal layers. Within this figure, the contents of the reservoir (i.e. local anesthetic, vasoconstrictor, anti-histamine, etc.) are diffusing 19 into the epidermis, dermis, and subdermal layers of the skin. The diffused contents of the reservoir act on the nerves 18 and blood vessels 17 around the transdermal delivery device.

Figure 3:
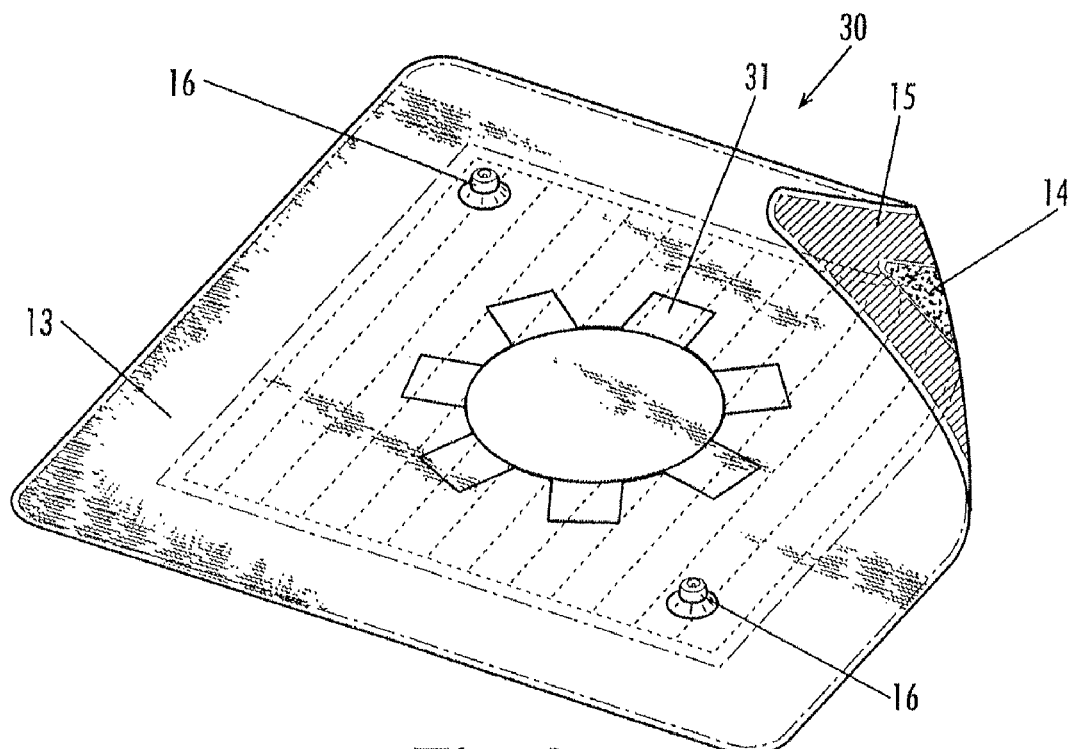
FIG. 3 shows the top view of a transdermal delivery device with multiple injection ports, two resealable refill ports, and an anesthetic reservoir.

FIG. 3 depicts a variation of the device 10 in FIG. 1. Referring to FIG. 3, device 30 has a seven injection ports 31. This device can be used for injection seven consecutive times. These injections may occur within one day or over a period of several days. Although not shown, an optional tether may be placed on the underside of the patch. This tether is a thin string made of metal, synthetic plastic, or semi-synthetic plastic which may connect the injection ports to one another. This tether functions to support each injection port and to prevent any resealable injection port from being dislodged or dislocated while removing a device such as a needle or lancet from the resealable injection port.

Figure 4:
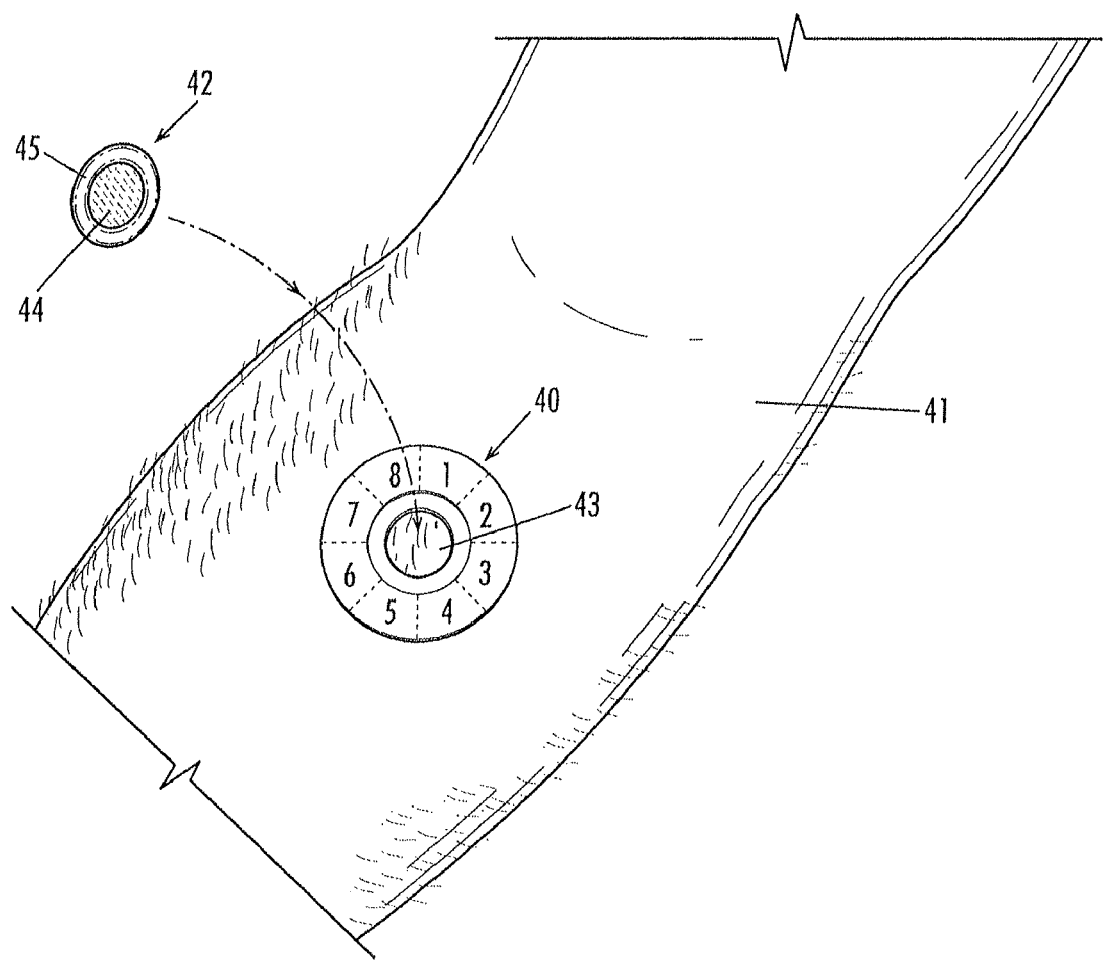
FIG. 4 shows a transdermal delivery device with a replaceable button with and an injection port having multiple adjacent resealable injection regions.

FIG. 4 provides another example of a delivery device having multiple injection ports in a circle so that the injection sites are rotated. Referring to FIG. 4, the device is composed of resealable injection port 40, which is shown as attached to the skin 41 of the subject, and a replaceable anesthetic button 42. The resealable injection port 40 as shown in FIG. 4 has eight injection regions, which means that the device can be used eight times before discarding the injection port 40. The injection port 40 can have an adhesive on the backside so that it can be affixed to the skin of the subject for extended periods of time. The resealable injection port 40 has an opening 43 for receiving the replaceable anesthetic button 42. The top and sides of the button are composed of an impermeable material, while the underside of the button that is in contact with the skin is composed of a permeable material. The impermeable and permeable materials described above can be used to produce the button 42. An adhesive is present on the surface 45 of the button, which helps adhere the button to the skin prior to injection. The volume of anesthetic present in the button will vary on the dimension of the button. In general, when the subject is ready to perform an injection, the replaceable anesthetic button is inserted into the injection port 40 for a sufficient time to numb the desired region of skin. An injection may be administered to injection region number one. When the next injection is administered, injection region number two will be used, and this will occur until all eight injection regions are used. The number of injection regions is not limited in number. After the injection, the replaceable anesthetic button is removed for future use. The injection port 40 can remain on the skin of the subject until all of the injection regions have been used.

Figure 5:
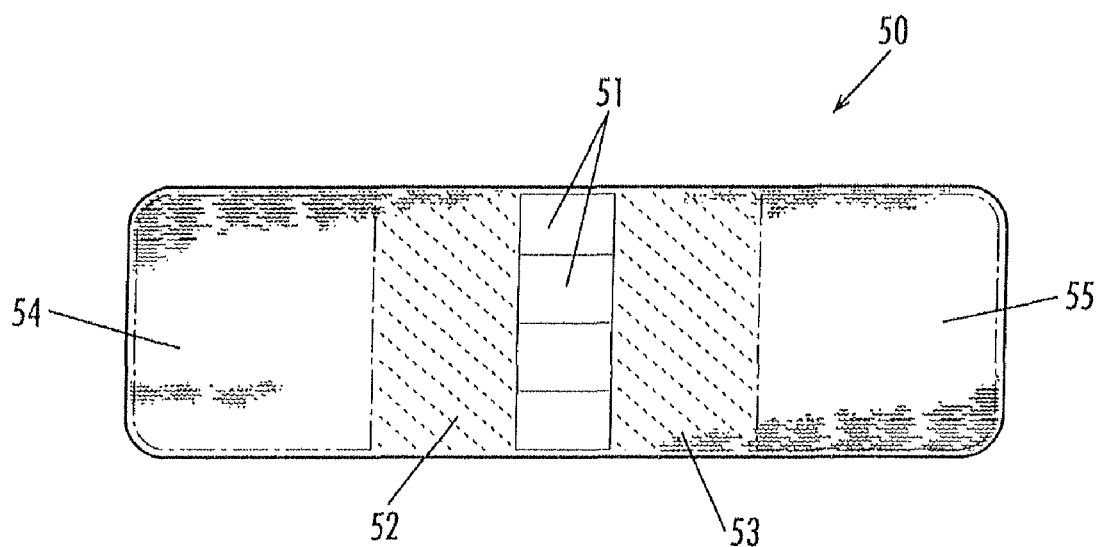
FIG. 5 shows a transdermal delivery device with multiple resealable injection ports surrounded by two anesthetic reservoirs without local anesthetic refill ports.
Figure 6:
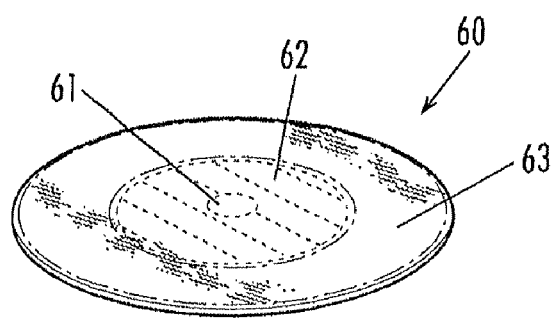
FIG. 6 shows a transdermal delivery device with a single resealable injection port surrounded by an anesthetic reservoir without a local anesthetic refill port.

FIGS. 5 and 6 depict additional devices described herein. As drawn, neither device has a resealable refill port for the local anesthetic; however, these features can easily be added by one of ordinary skill in the art, if desired. FIG. 5 shows the underside of device 50 (i.e., the side that is applied to the skin). The device 50 is composed of four resealable injection ports 51. In this aspect, anesthetic reservoirs 52 and 53 are adjacent to the injection ports. An adhesive can be applied to the surfaces 54 and 55, which are composed of an impermeable material. Although not shown in FIG. 5, a protective cover can be applied to the underside of the device 50 (and any of the other devices described herein) to prevent the anesthetic from leaking as well as decontamination of the injection port. The protective cover can be readily peeled off of the device 50 prior to use.

FIG. 6 shows another design of the delivery device. The underside of device 60 as shown in FIG. 6 has a resealable injection port 61 surrounded by an anesthetic reservoir 62, where the anesthetic can diffuse from the reservoir to the surface of the skin through a permeable or semipermeable membrane. An adhesive is applied to the surface 63. The surface 63 and the backside of device 60 are composed of an impermeable material.

Figure 7:
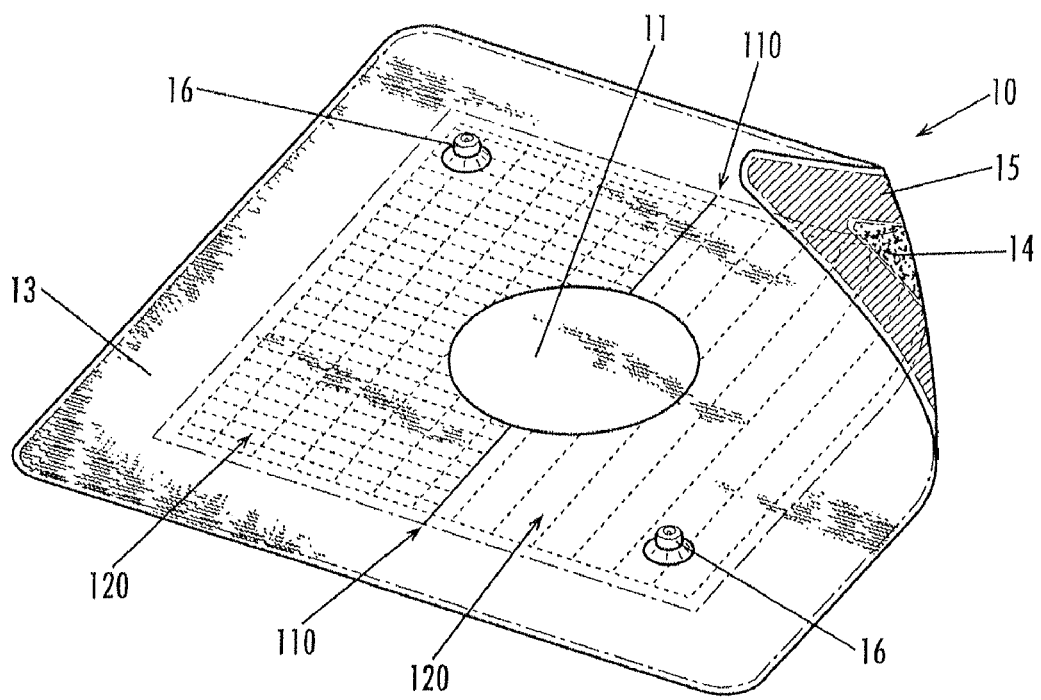
FIG. 7 shows the top view of a transdermal delivery device with a single injection port, two resealable refill ports, and a compartmentalized reservoir.

In FIG. 7, the transdermal delivery device 10 is a patch having at least one resealable injection port 11 and a compartmentalized reservoir 120. The reservoir may be divided by a dividing material 110 and form 1, 2, 3, 4, or any number of desired compartmentalized reservoirs 120. Each compartmentalized reservoir may contain either a single anesthetic or a single pharmaceutically acceptable preparation described herein, or the compartmentalized reservoir may contain a mixture of a local anesthetic or any other pharmaceutically acceptable preparation described herein. For example, within FIG. 7, the grid-like dashes within one compartmentalized reservoir 120 indicates the presence of a separate anesthetic, pharmaceutically acceptable preparation, biologic, or nutriceutical when compared with the other compartmentalized reservoir 120 having only vertical dashes. These pharmaceutically acceptable preparations, biologics, or nutriceuticals include but are not limited to local anesthetic agents, different therapeutic agents, different vasoconstrictors, different antiseptic agents, different antimicrobial agents, different antifungal agents, different antiviral agents, different skin permeability enhancers, different anti-inflammatory agents, or any combination thereof. On the topside of the device 10, an impermeable substrate 13 surrounds the injection port 11 and prevents the local anesthetic from leaching out of the reservoir. On the underside of the device 10, which is the side that is applied to the surface of the skin, an opposing permeable layer 14 is present and positioned under the reservoir 120. The permeable layer permits the diffusion of the local anesthetic from the reservoir to the skin surface. The permeable layer 14 is surrounded by an impermeable material 15, which prevents the local anesthetic from leaching to the sides of the device 10. An adhesive can be applied to the impermeable material 15, which helps adhere the device to the subject's skin. Semipermeable and permeable membranes may include, but are not limited to, materials made from regenerated cellulose, regenerated cellophane, cellulose ester membranes, charge mosaic membranes, bipolar membranes, amphoteric exchange membranes, anion exchange membranes, dialysis tubing, ethylene-vinyl acetate (EVA) copolymer membranes (e.g. 1-20% vinyl acetate), polyvinylalcohol (PVA) gels, or silicon films.

The device as shown in FIG. 7 also permits refilling of the reservoir 120 with local anesthetic or other therapeutic pharmacological agents, biologics, and nutriceuticals once the anesthetic, the therapeutic pharmacological agents, the biologics, and/or nutriceuticals have substantially or completely diffused from the compartmentalized reservoir. Resealable refill ports 16 may be present in the device 10. If present, the number of refill ports 16 may vary. In addition, the number of injection ports 11 may vary also. For example, with smaller devices, the refill port can be composed of a polymeric material such as that used in the injection port, which permits the injection of additional anesthetic or pharmaceutically acceptable preparation into the reservoir without a refill port. Thus, if desired, the delivery device depicted in FIG. 7 can be modified for multi-use or single use purposes further described herein.

Figure 8:
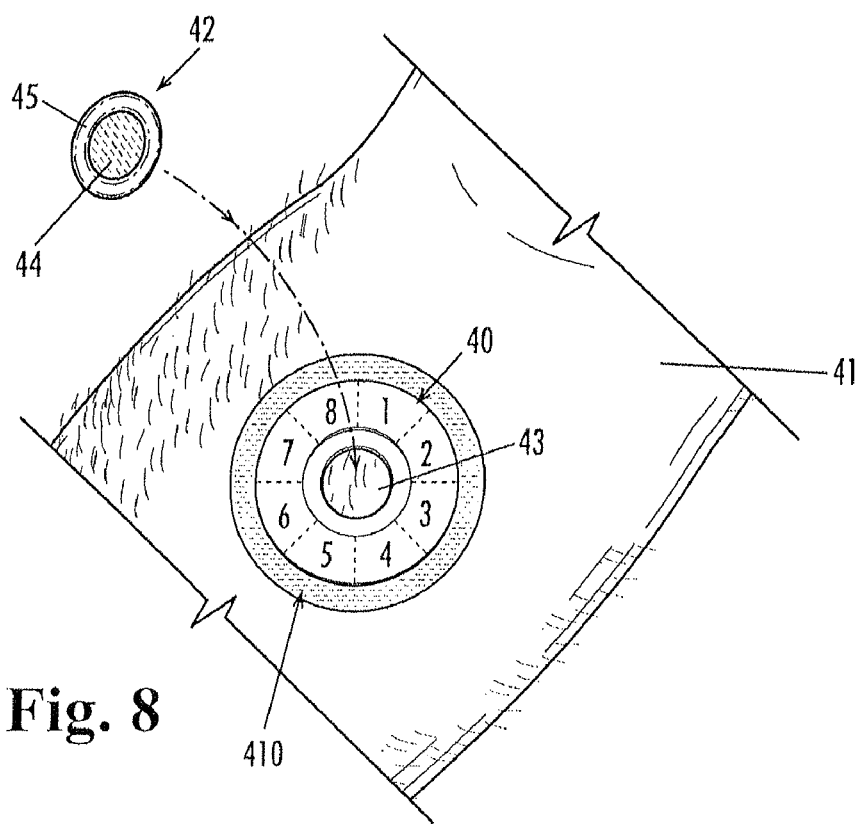
FIG. 8 shows a transdermal delivery device with a replaceable button, an injection port having multiple adjacent resealable injection regions, and a reservoir surrounding the resealable injection regions.

FIG. 8 provides another example of a delivery device having multiple injection ports in a circle so that the injection sites are rotated. Referring to FIG. 8, the device is composed of resealable injection port 40, which is shown as attached to the skin 41 of the subject, and a replaceable anesthetic button 42. The resealable injection port 40 as shown in FIG. 8 has eight injection regions, which means that the device can be used eight times before discarding the injection port 40. The injection port 40 can have an adhesive on the backside so that it can be affixed to the skin of the subject for extended periods of time. The resealable injection port 40 has an opening 43 for receiving the replaceable anesthetic button 42. The top and sides of the button are composed of an impermeable material, while the underside of the button that is in contact with the skin is composed of a permeable material. The impermeable and permeable materials described above can be used to produce the button 42. An adhesive is present on the surface 45 of the button, which helps adhere the button to the skin prior to injection. The volume of anesthetic present in the button will vary on the dimension of the button. In general, when the subject is ready to perform an injection, the replaceable anesthetic button is inserted into the injection port 40 for a sufficient time to numb the desired region of skin. An injection may be administered to injection region number one. When the next injection is administered, injection region number two will be used, and this will occur until all eight injection regions are used. The number of injection regions is not limited in number. After the injection, the replaceable anesthetic button is removed for future use. The injection port 40 can remain on the skin of the subject until all of the injection regions have been used. Also, a compartmentalized reservoir 410 may surround the injection ports. This reservoir may be a single reservoir or divided into two, three, four, or any number of desired compartments. Each compartmentalized reservoir may contain either a single anesthetic or pharmaceutically acceptable preparation described herein, or the each compartmentalized reservoir may contain a mixture of a local anesthetic or any other pharmaceutically acceptable preparation described herein such as hormones, nicotine, vitamins, narcotics, nutriceuticals, anti-Alzheimer's medication, Parkinson's medication, autism medication, and various other medications used to treat neurological diseases, anti-tumor necrosis factors, anti-tumor agents, heart medications, or various other transdermally transportable therapeutic agents described herein or known to one of ordinary skill in the art the for prevention and treatment of local and systemic diseases.

The optional therapeutic agents described above can be incorporated in a number of different locations within the delivery device. For example, an antiseptic agent can be applied to the surface of the injection port (topside and/or underside) to kill any bacteria, virus, or fungus that may be present on the syringe and maintain a sterile environment at the injection site. Alternatively, in order to maintain a sterile environment at the injection port, the injection port can be covered with an antiseptic cap or cover. In other aspects, one or more therapeutic agents can be mixed with the anesthetic and the mixture introduced into the anesthetic reservoir. In this aspect, the therapeutic agent diffuses to the skin with the anesthetic.

The devices described herein can be applied to the skin of a subject where the skin is ultimately going to be punctured in order to reduce or eliminate pain associated with the puncture. The underside of the injection port(s) has non irritating adhesive which will facilitate sticking to the skin when applied. Such adhesive may include a topical silicone adhesive, a water based adhesive, epoxies, urethanes, methacrylates, polyacrylates, rubber-based adhesives, polysiloxane adhesives, pressure sensitives, starches, and phenolics of varying tack levels depending on the subject's skin and the task at hand. The adhesive material may be an acrylic adhesive including at least one polymer selected from homopolymers of acrylic esters, copolymers of two or more types of acrylic ester units and copolymers of acrylic esters and other functional monomers. Acrylic esters include, but are not limited to, butyl(meth)acrylate, pentyl(meth)acrylate, hexyl (meth)acrylate, heptyl(meth)acrylate, octy(meth)acrylate, nonyl(meth)acrylate, decyl(meth)acrylate. Functional monomers include, but are not limited to, monomers containing a hydroxyl group, such as hydroxyethyl(meth)acrylate, hydroxypropyl(meth)acrylate, monomers containing a carboxyl group such as carboxyl methacrylate and monomers containing an amide group such as methacrylamide, dimethylmethacrylamide, etc.

Specific examples of acrylate monomers, which are suitable for use with the present invention include, but are not limited to methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, dodecylmethacrylate, tridecyl acrylate, tridecyl methacrylate, and mixtures thereof.

Specific examples of functional monomers which are copolymerizable with the above-recited alkyl acrylates or methacrylates, which can also be used include, but are not limited to acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, and mixtures thereof.

Specific examples of suitable rubber-based pressure sensitive adhesives include but are not limited to hydrocarbon polymers, such as natural and synthetic polyisoprenes, polybutylenes, polyisobutylene (PIB), styrene/butadiene polymers, styrene-isoprene-styrene block copolymers, hydrocarbon polymers such as butyl rubber, halogen-containing polymers such as polyacrylic nitrile, polytetrafluoroethylene, polyvinyl chloride, polyvinylidene chloride, and polychlorodiene, and polysiloxane, and other copolymers thereof.

Specific examples of polysiloxanes include but are not limited to silicone pressure sensitive adhesives, which are based on two major components: a polymer, or gum, and a tackifying resin. The polysiloxane adhesive may be prepared by cross-linking the gum, typically a high molecular weight polydiorganosiloxane with the resin to produce a three-dimensional silicate structure via a condensation reaction in an appropriate organic solvent. Various aspects of formulating polysiloxane adhesives are known in the art. Suitable silicone pressure-sensitive adhesives are commercially available and include the silicone adhesives sold as BIO-PSA®, Dow Corning Corporation, Medical Products, Midland, Mich.

As described above, the local anesthetic diffuses from the anesthetic reservoir onto the skin. The local anesthetic numbs a portion of the skin at or near the injection site. The duration of contact between the skin and the anesthetic can vary depending upon the type of puncture or injection that is made. In one aspect, the device is applied 30 to 60 minutes in advance to allow the local anesthetic to enter the dermal never fibers in the skin and block them so that when the injection occurs, the subject does not feel pain. The devices described herein have numerous applications including, but not limited to, reducing or eliminating pain associated with the injection of bioactive agents such as drugs and both pediatric and adult vaccines; the drawing of blood from a subject; the use of permanent infusion ports; the use of artery-venous (A-V) shunts used in kidney dialysis; the use of ports to inject various steroids and other therapeutic agents into the diseased or damaged tissue such as muscles, tendons, and joints; their use by podiatrists for corns; their use as a band aid to draw the blood droplets to test for glucose levels in diabetics and other blood chemistry analysis; and the insertion of cannulas for intravenous infusion, catheters, PICC lines for long IV infusions, Swan Ganz catheter intersection, nerve blocks to relive pain, and injections of painful joints.

The transdermal transport of a local anesthetic and a therapeutic agent is enhanced by the application of a secondary driving force either before or after application of the transdermal delivery device. In certain aspects this secondary driving force includes electromotive (electrotransport) force in the form of iontophoresis, electroosmosis, electroporation, fractional laser; or mechanical force such as magnetic force, vibration, vibroacoustic force, or sonophoretic force such as ultrasound. This force may be applied to enhance the uptake of the local anesthetic into subcutaneous tissue for rapid blocking of pain conduction nerve endings. For example, without wishing to be bound by theory, when ultrasound is used, low frequency is used. In one aspect, less than 2.5 MHz is used. In yet another aspect, less than 1 MHz is used. When acoustical vibrations (low frequency ultrasound with vibration—Vibroacoustic) are applied using a specified pulse ranging, from one-half second to three seconds, modulated with an oscillatory signal in the frequency range of 1 Hz to 1500 Hz, and having pulse amplitude in the range of about 20 to 5000 microns, transdermal transport of a local anesthetic and a therapeutic agent may be further enhanced.

The application of the electromotive force can be applied to the skin prior to and/or after the application of the transdermal delivery device. In one aspect, an electromotive force such as, for example, ultrasound, can be applied to the skin first for a sufficient time. Next, the transdermal delivery device can be applied to the skin where the ultrasound was applied. Finally, ultrasound can be applied to the delivery device such as transdermal local anesthetic patch port or other various known therapeutic agents, as well as other pharmaceutical, biochemical, nurticeuticals, and biological agents or compounds therapeutic agents delivery patch. Details regarding these embodiments are described in greater detail below.

In certain aspects, a therapeutic device for blocking pain in a subject's digit and includes a ring-like vibratory part adapted to be fitted about the digit temporarily. A controller is coupled to the ring-like vibratory part for controlling operation of the ring-like vibratory element. By applying vibration to the subject's digit, pain transmission is blocked or lessened along the digit, allowing the subject or a caregiver to provide treatment to the digit with reduced pain. For example, the invention can be applied to a finger prior to sticking the finger (as for drawing blood, for example, for a blood sugar measurement). Moreover, if the digit is injured, the present invention can provide pain relief from the injury as well. Further, the invention can be applied to the digit in combination with other pain-reducing therapies, such as the application of ice, the application of topical analgesics, the application of local anesthetics, etc.

The vibratory element can be selected or adapted to induce vibrations at different frequencies, as desired, including subsonic, sonic, and ultrasonic frequencies.

Optionally, the ring-like vibratory element includes a first section and a second section hingedly coupled to the first section at first ends thereof. Preferably, the first and second sections of the ring-like vibratory element are each generally C-shaped. Preferably, an openable closure is provided for selectively securing second ends of the first and second sections to one another. In one form, the openable closure comprises a hook and loop fastener for releasably securing the second ends of the first and second sections to one another.

Optionally, the ring-like element can include an inner elastic loop instead of a vibratory element to be slipped around a digit and one or more vibratory motors mounted to the outside of the inner elastic loop.

Optionally, an elastic element can be provided for elastically securing second ends of the first and second sections to one another. Additionally, a second elastic element can be provided so that both the first and second ends of each section are elastically secured to one another. Furthermore, a clasp-like element can be provided for releasably securing second ends of the first and second sections to one another.

Optionally, the vibrations can be ultrasonic or a combination of ultrasonic and non-ultrasonic vibrations.

Optionally, the controller includes an on/off control switch and a switch for controlling the vibratory frequency. Preferably, the controller includes a battery power source for powering the ring-like vibratory element. Also preferably, the ring-like vibratory element includes an electrically-powered vibratory motor for creating vibrations in the digit.

The ring-like vibratory element can be adapted to apply vibrations (including ultrasonic) to an entirely circumferential region of the digit (all the way around the digit) or can be adapted to apply vibrations to just selected regions of the digit. In this regard, it is noted that typically the nerve bundle extending within and along the digit tend to be positioned in specific, known locations such that the ring-like vibratory element can be adapted to apply vibratory energy adjacent the nerve bundles, while leaving other portions of the digit be as is. In other words, the ring-like vibratory element can be adapted to target the nerves.

One good example of a ready application for the present invention is a digital vibrator to reduce needle or lancing pain at the finger, thumb, or toes, such as when used to get a blood sample to test for blood sugar levels and other laboratory tests. This is particularly helpful for diabetics in that they often have to stick themselves in the digits repeatedly, often several times per day. Many diabetics find this painful and have to endure such pain many times per day. The present invention can provide substantial relief to such subjects, for example.

The present invention can also be used in conjunction with a local anesthetic port patch to enhance the uptake of local anesthetics from the patch from the surface of the skin. The vibrator can also induce numbness on its own.

In another preferred form the invention comprises a method for blocking pain in a subject's digit and includes the steps of: (a) securing a pair of vibratory and/or ultrasonic elements to the subject's digit, positioned on opposite sections of the digit along the nerve bundles, the vibratory elements adapted and sized for vibrationally stimulating opposite sides of a subject's digit; and (b) operating the vibratory and/or ultrasonic elements by a controller coupled to the vibratory elements.

Preferably, these steps (a, b) are carried out prior to a needle stick in the subject's digit. Also preferably, before the needle stick takes place, one applies a local anesthetic to a portion of the subject's digit to be subjected to the needle stick. In one preferred form, the step of applying a local anesthetic comprises applying a transdermal delivery device described herein to the subject's digit, the patch being adapted to deliver an anesthetic locally to the digit.

These methods combined will have augmentation—amplification effects to relieve the pain of needle sticks for any and all therapeutic applications such as injection of therapeutic agents and vein or arterial access for any and all medical applications.

Such a device and method according the invention is reusable, practical, easy to clean, usable in all age groups, can operate with a rechargeable or disposable battery (or batteries), and is not be cumbersome to use. Moreover, the digital vibration device (DVD) described herein can be used with or without the use of a transdermal local anesthetic patch port. Furthermore, the digital vibration device can be used with a local anesthetic band aid. It can also be used for these needs and others to take away pain in situations such as removing splinter, burns, or injury to fingers, nails, any and all painful conditions that the present invention is aimed at.

Not wishing to be bound by theory, the present invention is believed to helps to reduce pain and induce analgesia based on the "gate" theory of pain. Based on gate theory, vibration helps to reduce pain as the vibration of cutaneous nerves send impulse to the spinal cord gate and block the gate and prevents the higher center receiving the pain impulses. The transdermal local anesthetic patch port on the other hand works differently, and its analgesic—anesthetic effects are local. It stops pain by blocking the sodium and potassium channels needed to generate nerve impulse. It is local and entirely different mechanism form the vibration method of inducing analgesia. That is why, the pain relief by using a vibration device is analgesic, meaning reducing the feeling the sensation of pain, not complete anesthesia as seen in the transdermal local anesthetic patch port.

The theory behind the pain relief of the present invention is believed to be consistent with Melzack and Wall's gating mechanism within the spinal cords. The pain gate is closed in response to normal stimulation of the fast conducting "touch" possibly vibration nerve fibers (vibration stimulation); but opened when the slow conducting "pain" fibers transmitted a high volume and intensity of sensory signals. The gate could be closed again if these signals were countered by renewed stimulation of the large fibers (Ronald Melzack and Patrick Wall "Pain Mechanisms: A New Theory," Science: 150, 171-179, 1965). Those authors proposed that thin ("pain") and large diameter ("touch, pressure, vibration") nerve fibers carry information from the site of injury to two targets in the dorsal horn of the spinal cord: the "inhibitory" cells and the "transmission" cells. Signals from thin and large diameter fibers excite the transmission cells, and when the output of the transmission cells exceeds a critical level, pain begins. The job of the inhibitory cells is to inhibit activation of the transmission cells and shut the gate. When thin (pain) and large (touch, etc) fibers, activated by a noxious event (lancing, needle sticks), excite a spinal cord transmission cell, they also act on its inhibitory cells. The thin fibers impede the inhibitory cells (tending to leave the gate open) while the large diameter fibers excite the inhibitory cells (tending to close the gate-vibration sense). So, the more large fiber activity relative to thin fiber activity coming from the inhibitory cell's receptive field, the less pain is felt. Vibration induces analgesia by partially closing the gate through the large fibers.

Pain signals can also travel from the site of injury directly up the cord to the brain (bypassing the inhibitory and transmission cells) where, depending on the state of the brain, it may trigger a signal back down the spinal cord to modulate inhibitory cell activity (and so pain intensity). This was the first theory to offer a physiological explanation for the previously reported effect of psychology on pain perception. Perception and blocking of the pain is very complicated. The vibration activates large nerve fibers first, then small pain fibers, thus inhibiting the pain at the site of lancing or injection by shutting the pain gate in the spinal cord. It is only partial closure that is why there is analgesia, not complete anesthesia as seen by use of a transdermal local anesthetic patch port. That is why the combination used of a vibratory device and a transdermal local anesthetic patch port is effective in relieving the acute pain due to needle stick of any kind and lancing effectively in rapid succession.

Figure 9:
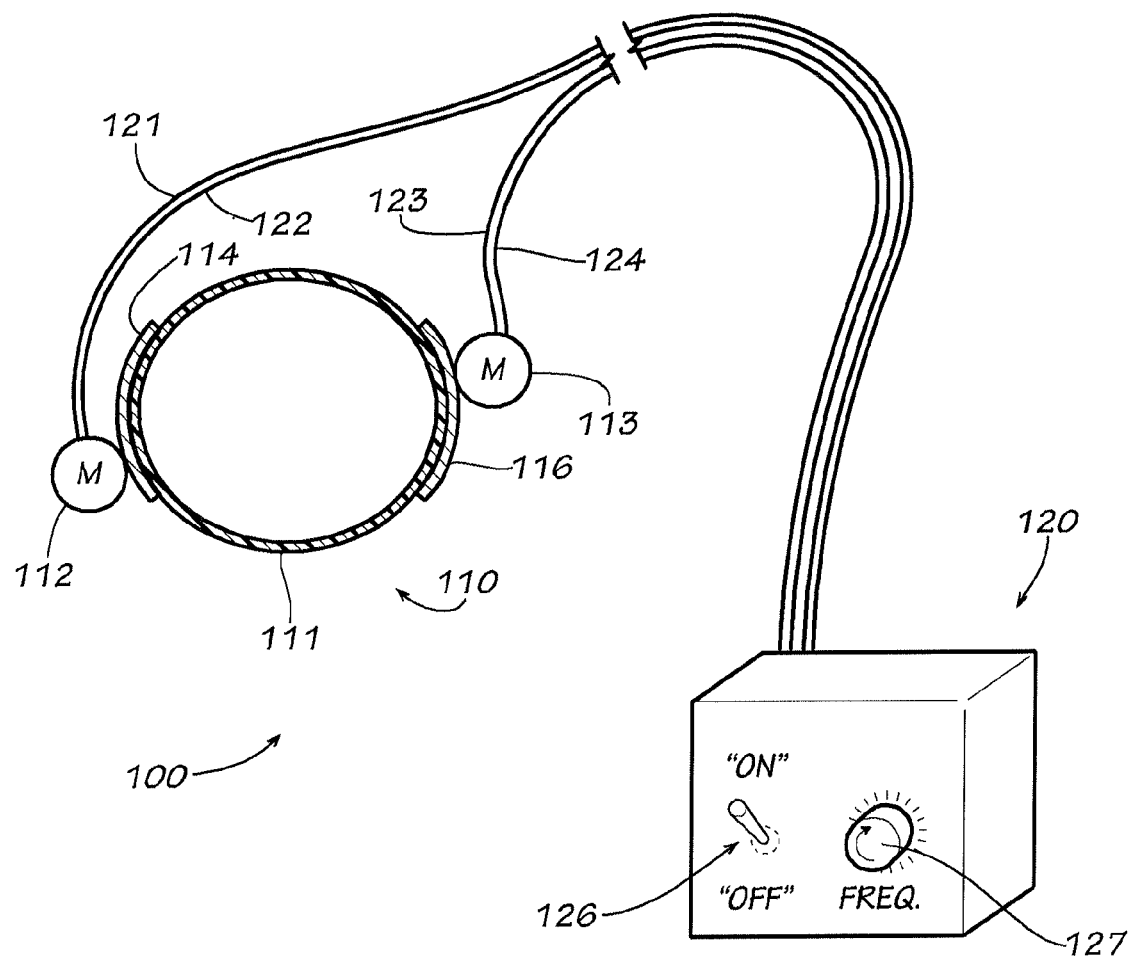
FIG. 9 is a schematic illustration of a therapeutic device for blocking pain in a subject's digit according to a first preferred form of the invention, showing a ring-like vibratory part and a control box/power supply.

FIG. 9 is a schematic illustration (not to scale) of a therapeutic device 100 for blocking pain in a subject's digit according to a first preferred form of the invention, showing a ring-like vibratory part 110 and a control box/power supply 120. The ring-like vibratory part 110 is adapted to be fitted about the subject's digit temporarily. The controller or control box 120 is coupled to the ring-like vibratory part for controlling operation of the ring-like vibratory element 110 with electrical wires, here two pairs of wires 121-124. By applying vibration to the subject's digit, pain transmission is blocked or lessened along the digit, allowing the subject or a caregiver to provide treatment to the digit with reduced pain. The vibratory element 110 and the controller 120 can be selected or adapted to induce vibrations at different frequencies, as desired, including subsonic, sonic, and ultrasonic frequencies.

In this first example form shown, the ring-like vibratory element 110 can include an inner elastic loop 111 adapted to be slipped around a digit and one or more vibratory motors 112, 113 mounted to the outside of the inner elastic loop. As shown, thin metal strips 114, 116 are bonded to the elastic loop for supporting the vibratory motors and transmitting vibrations to the thin elastic loop.

Optionally, the controller 120 includes an on/off control switch 126 and a rotary switch 127 for controlling the vibratory frequency. Preferably, the controller 120 includes a battery power source for powering the ring-like vibratory element. Alternatively, instead of using a battery to power the controller 120, the controller can be provided with a 120 VAC plug for plugging into a wall outlet. Typically, the motors 112, 113 will be DC motors such that the controller 120 would then have an AC-to-DC converter to supply the vibratory elements with DC current.

Figure 10:
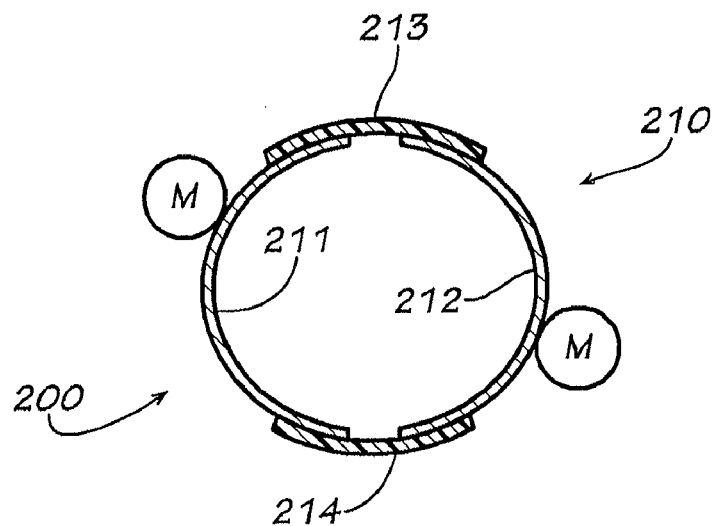
FIG. 10 is a schematic illustration of a therapeutic device for blocking pain in a subject's digit according to another preferred form of the invention, showing a ring-like vibratory part and omitting a control box/power supply for simplicity of illustration.

FIG. 10 is a schematic illustration of a therapeutic device 200 for blocking pain in a subject's digit according to another preferred form of the invention, showing a ring-like vibratory part and omitting a control box/power supply for simplicity of illustration. In this embodiment, the controller is as above, so its description is not repeated herein. In this embodiment, the ring-like vibratory element 210 includes two arcuate metal strips 211, 212 coupled together by a pair of flexible elements 213, 214. The flexible elements 213, 214 can be rubber strips as depicted or can be fabric. Elasticity in these elements, along with some torsional flexibility, will facilitate the mounting of the ring-like vibratory part 210 over the subject's digit (finger or toe). In this regard, the elasticity allows the device to be slipped over the digit by simply stretching action. As above, the metal strips 211, 212 bear vibratory motors that impart vibration to the metal strips.

Figure 11:
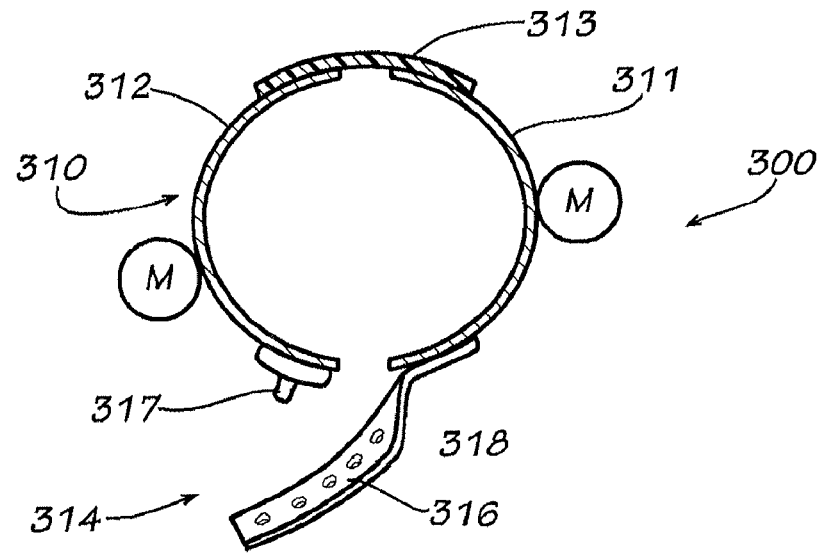
FIG. 11 is a schematic illustration of a therapeutic device for blocking pain in a subject's digit according to another preferred form of the invention, showing a ring-like vibratory part and omitting a control box/power supply for simplicity of illustration.

FIG. 11 is a schematic illustration of a therapeutic device 300 for blocking pain in a subject's digit according to another preferred form of the invention, showing a ring-like vibratory part 310 and omitting a control box/power supply for simplicity of illustration. In this embodiment, the ring-like vibratory element 310 includes two arcuate metal strips 311, 312 coupled together by a flexible element 313 and a closure 314. The flexible element 313 acts as a sort of hinge and can be a rubber strip as depicted or can be fabric. The closure 314 is in the form of a hasp, much like a buckle and includes a flexible elongate portion 316 bonded to the metal strip 311 and a post-like portion 317 bonded to the metal strip 312. The flexible elongate portion has a series of perforations, such as perforation 318, formed therein for receiving the post therethrough at different positions, thereby allowing for some adjustability in the size of the digit to be encircled. To place the device on a digit, one opens the closure 314 and opens the ring-like element and slips the device over the digit. Once over the digit, one can close the closure by engaging the post through one of the perforations. As above, the metal strips 311, 312 bear vibratory motors that impart vibration to the metal strips.

Figure 12:
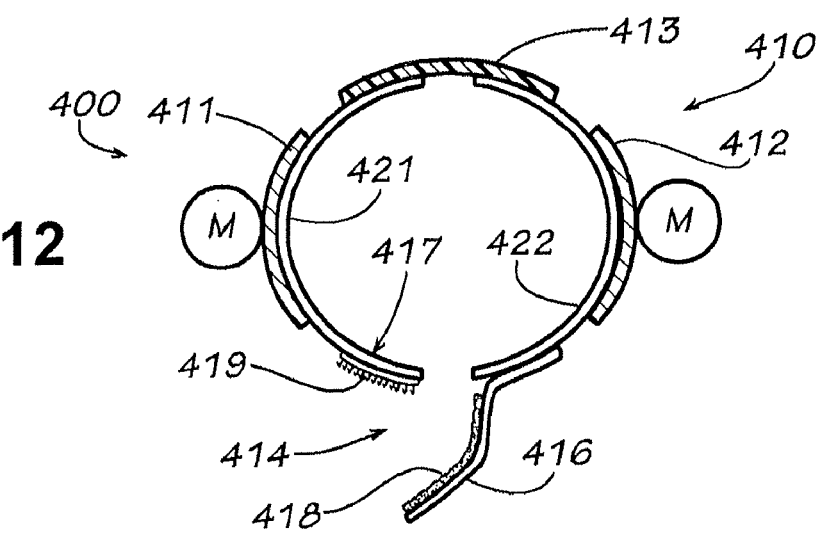
FIG. 12 is a schematic illustration of a therapeutic device for blocking pain in a subject's digit according to another preferred form of the invention, showing a ring-like vibratory part and omitting a control box/power supply for simplicity of illustration.

FIG. 12 is a schematic illustration of a therapeutic device 400 for blocking pain in a subject's digit according to another preferred form of the invention, showing a ring-like vibratory part 410 and omitting a control box/power supply for simplicity of illustration. In this embodiment, the ring-like vibratory element 410 includes two arcuate metal strips 411, 412 coupled together by a flexible element 413 and a closure 414. The flexible element 413 acts as a sort of hinge and can be a rubber strip as depicted or can be fabric. The closure 414 is in the form of a hasp, much like a buckle and includes a flexible elongate portion 416 with one end bonded to the metal strip 412 and bearing hook and look fastener material 418 on a distal end. The closure 414 also includes a portion 417 bonded to the metal strip 411 and bearing hook and loop fastener material 419. The hook and loop fastener material can be attached to each other at different positions, thereby allowing for some adjustability in the size of the digit to be encircled. To place the device on a digit, one opens the closure 414 and opens the ring-like element and slips the device over the digit. Once over the digit, one can close the closure by engaging the post through one of the perforations.

Moreover, as shown in FIG. 12, an optional fabric or resilient liner 421, 422 can be attached to the inside of the metal strips 411, 412 to make the device more comfortable.

The ring-like vibratory elements described above can be adapted to apply vibrations to an entirely circumferential region of the digit (all the way around the digit) or can be adapted to apply vibrations to just selected regions of the digit. In this regard, it is noted that typically the nerve bundle extending within and along the digit tend to be positioned in specific, known locations such that the ring-like vibratory element can be adapted to apply vibratory energy adjacent the nerve bundles, while leaving other portions of the digit alone. In other words, the ring-like vibratory element can be adapted to target the nerves, as desired. In this regard, the split designs depicted herein showing two arcuate (C-shaped) metal strips are preferred as an effective way to target the nerve bundles in the digit.

Figure 13:
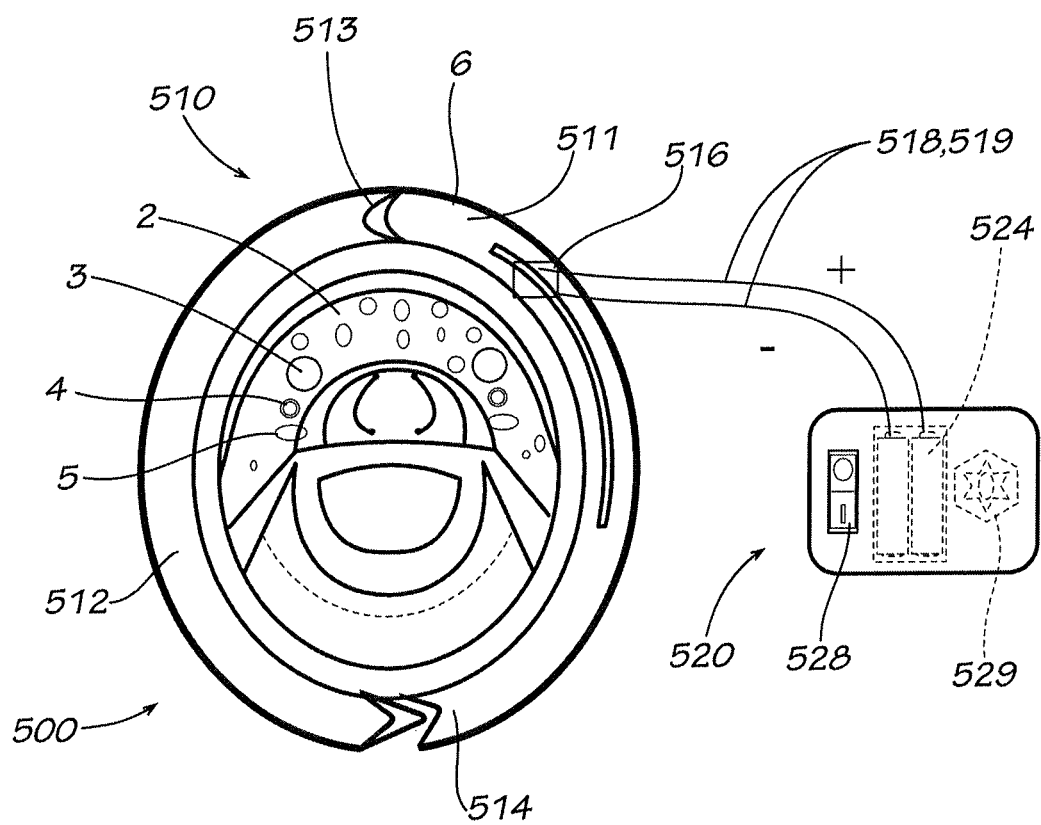
FIG. 13 is a schematic illustration of a therapeutic device for blocking pain in a subject's digit according to another preferred form of the invention, showing a ring-like vibratory part and a control box/power supply.

FIG. 13 is a schematic illustration of a therapeutic device 500 for blocking pain in a subject's digit according to another preferred form of the invention, showing a ring-like vibratory part 510 and a control box/power supply 520. FIG. 13 (as does FIG. 16) also shows the anatomy and histology of the finger cross section 100 showing the pulp of the finger which contains rich arteriovenous plexus and vast network of pain nerve fibers, where the lancing is performed to extract drops of blood to test for blood sugar and other laboratory parameters to maintain health and test for any physiological abnormality for diagnosis of disease. The diagram shows the pulp 2 of the fingers with rich BV plexus (circles) and nerves (black dots), digital nerve fasciculus 3 which supplies the pulp; digital artery 4 and digital vein 5 which join with each other at the pulp of the terminal digits to form rich vascular network. Pulp contains a rich network of terminal sensory nerve fibers and nerve endings which convey the pain, pressure, vibration, heat and cold sensations to the spinal cord and then to the central nervous system, such as due to penetration of a needle or lancets. It is from these blood vessels the blood is drawn by after lancing the pulp of the digits.

Moreover, as shown in FIG. 13, the digital (relating to anatomical digits, not digital as in digital electronics) vibrator device (DVD) 510 comprises a ring-like element to be wrapped around a digit, such as a finger or toe. As shown herein, the digital vibratory device includes a first C-shaped portion 511 hinged to a second C-shaped portion 512 at a hinge 513. A hook and loop fastener closure 514 is positioned opposite the hinge 513 and releasably secures ends of the C-shaped portions 511, 512 to each other.

Vibration is imparted in the ring-like element 510 by a vibrational motor 516 connected by power cables 518, 519 to a control box 520. The vibratory motor 516 can be activated to deliver 300 to 6000 vibrations per minute, according to the need and tolerability of the subject. The vibrations can be adjusted to the comfort level of the subject to obtain the maximum pain relief within a minimum time. The vibration can be set, for example, to 300, 500, 750, 1000, 1500, 2000, 3000, 4000, 5000 or 6000 vibrations per minute. Of course, these frequencies are just examples and other frequencies can be chosen. The vibration motor 516 can be switched between vibration cycles by a potentiostatic switch 529 or other mechanism. The vibration motor 516 can be varied continuously or step-wise between 300 vibrations per minute and 6000 vibrations per minute using the potentiostatic switch 529. The power to operate the vibrator is provided by the battery pack 524 connected by positive and negative wires. The power switch 528 to turn on the vibrator is located on the housing of the control box 520 (also can be referred to as a battery pack).

The power source 524 can be any of well-known battery technologies, including conventional alkaline, NiCad, lithium ion, or nickel metal hydride batteries or other battery types. The batteries or battery can be rechargeable or not, as desired. Moreover, instead of using a battery, a continuous source of electric power can be employed, such as 120 VAC from wall outlet. If a rechargeable energy pack is used, optionally one may also include a recharger base.

Switch 528 can be a regular, ordinary on/off switch, such as a toggle, lever, push-button, capacitance or other switch. Switch 529 can be eliminated and instead its function can be automatically incorporated in the control box which would then vary the vibration cycle of the motor. The switch 529 can be implemented as a common potentiostat. This category of control switch 529 would be functional with a vibration motor that operates at many different vibration cycles.

Notice that the vibrator can be slipped on the digit as a ring or through the hinge arrangement 513 to open and attach the ring-like vibratory element to the digit. If the device is to be used to lessen or block pain for the lancing of a fingertip, as is common in blood sugar measurement, the device can conveniently be placed approximately an inch to an inch and a half from the very tip of the finger. The hook and loop fastener 514 holds the vibrator tightly in place.

Figure 14:
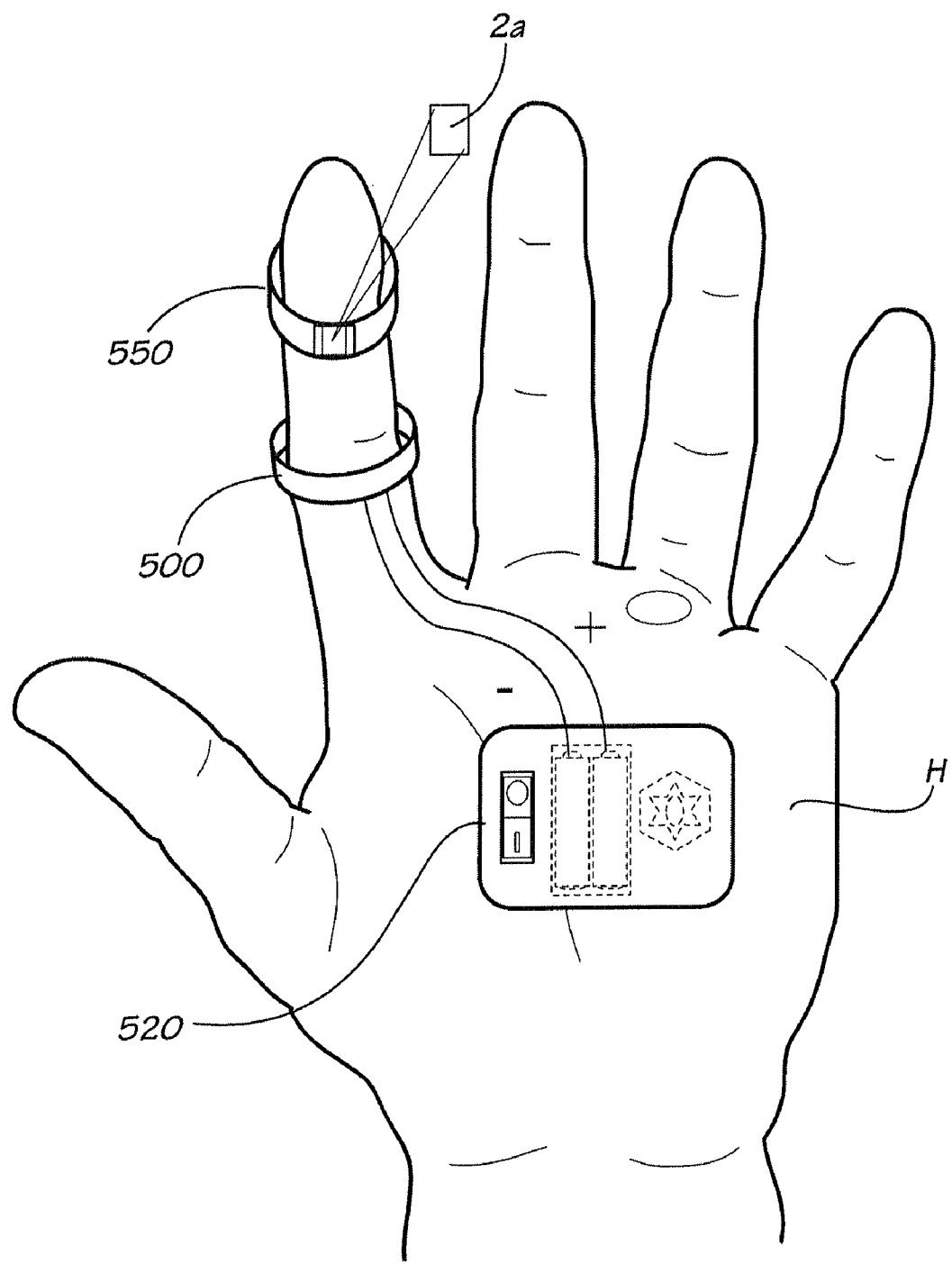
FIG. 14 is a schematic illustration of the therapeutic device of FIG. 13 for blocking pain in a subject's digit, showing a ring-like vibratory part positioned about a subject's digit and showing a control box/power supply in the palm of the subject's hand, and shown in conjunction with an optional anesthetic port band aid positioned toward a distal end on the digit.

FIG. 14 shows a DVD vibrator 500 placed on a digit of the hand H and local anesthetic port band aid 550 on the digit with the site to be lanced 2a. It shows the application of the transdermal local anesthetic patch port band aid 550 around the finger pulp with lancet entering the area 2a at the anesthetized band aid patch port. The lancet or needle is puncturing through this transdermal local anesthetic patch port to draw the blood. After drawing the blood, one need not have to apply a new band aid. This band aid 300 seals the skin puncture, maintaining sterility, and keeps the finger tip pain free for long time after the insult. The finger terminal pulp site can be accessed four times without pain with the transdermal local anesthetic patch port. The digital vibration device 500 (DVD) can be applied proximal to the transdermal local anesthetic patch 550, with controls of the device 520 placed in the palm of the hand. This can be activated for a minute or two or five or any length of time to obtain the maximum analgesia and anesthesia as the terminal digital pulp is accessed at 2a. The digital vibration devices 100, 200, 300, 400, 500, described above, can be used as shown in this figure.

Figure 15:
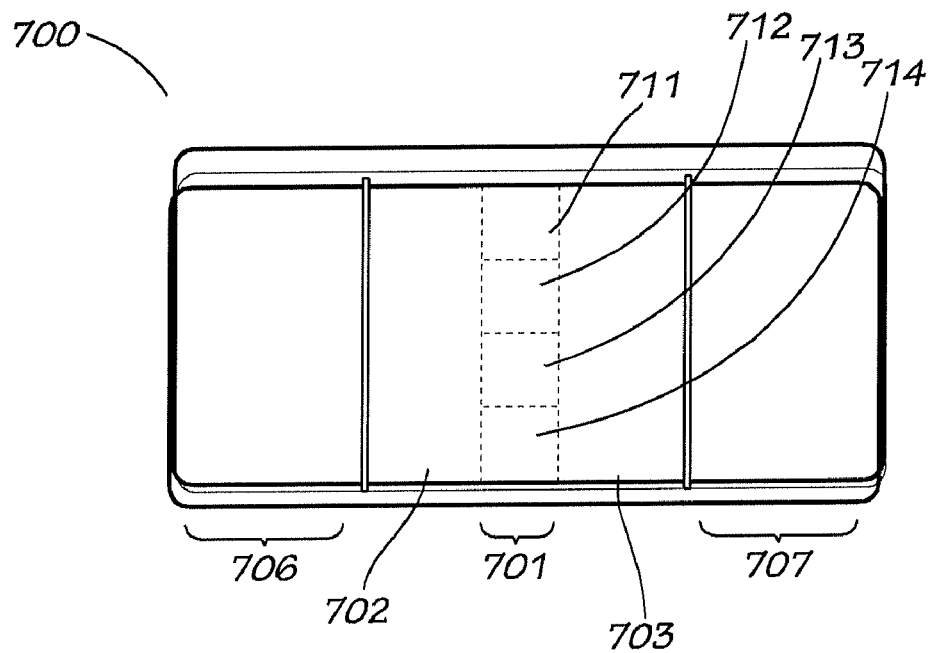
FIG. 15 is a schematic illustration of an optional anesthetic port band aid (transdermal patch) as shown in FIG. 14.

FIG. 15 is a schematic diagram of a transdermal local anesthetic patch (a port band aid) 700 and shows the underside of thereof (i.e., the side that is applied to the skin). The patch 700 includes a central region 701 flanked by two intermediate regions 702, 703, and two outer regions 706, 707. The central region 701 includes four resealable injection ports 711-714. In this respect, anesthetic reservoirs are formed in the intermediate regions 702, 703 and are adjacent to the injection ports 711-714 (flanking the injection ports). An adhesive can be applied to the surfaces in the outer regions 706, 707, which are composed of an impermeable material.

Although not shown in this figure, a protective cover can be applied to the underside of the transdermal local anesthetic patch 700 (and any of the other devices described herein) to prevent the anesthetic from leaking, as well as preventing contamination of the injection port. The protective cover can be readily peeled off prior to use. An adhesive can be applied to the surfaces which are composed of an impermeable material and can be easily peeled off.

Figure 16:
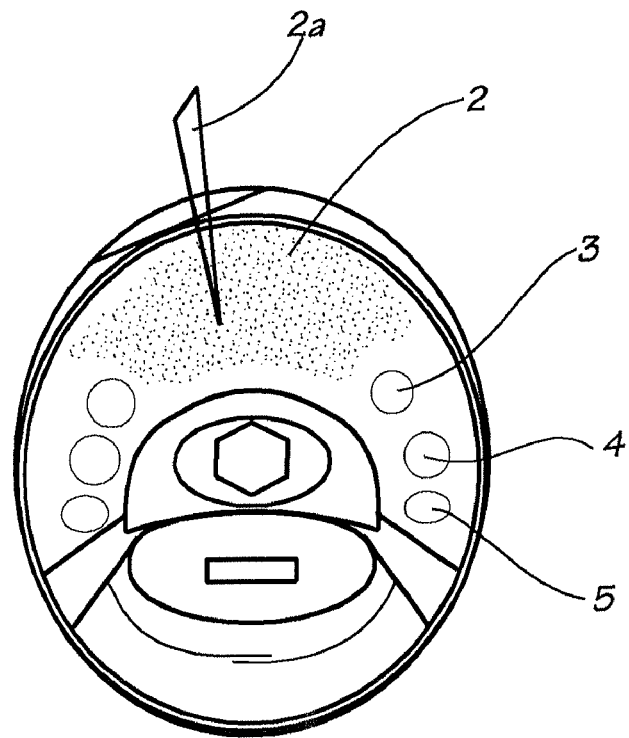
FIG. 16 is a schematic cross-section of a human digit, in particular a finger, and showing the anatomy and histology of the finger.

FIG. 16 is a schematic cross-section of a human digit, in particular a finger, and showing the anatomy and histology of the finger. Advantageously, the present invention takes advantage of the positions of the digital nerve 3, artery 4, and vein 5 in the finger, located at the 3 and 9 o'clock positions where the maximum vibration is concentrated from the DVD.

Figure 17:
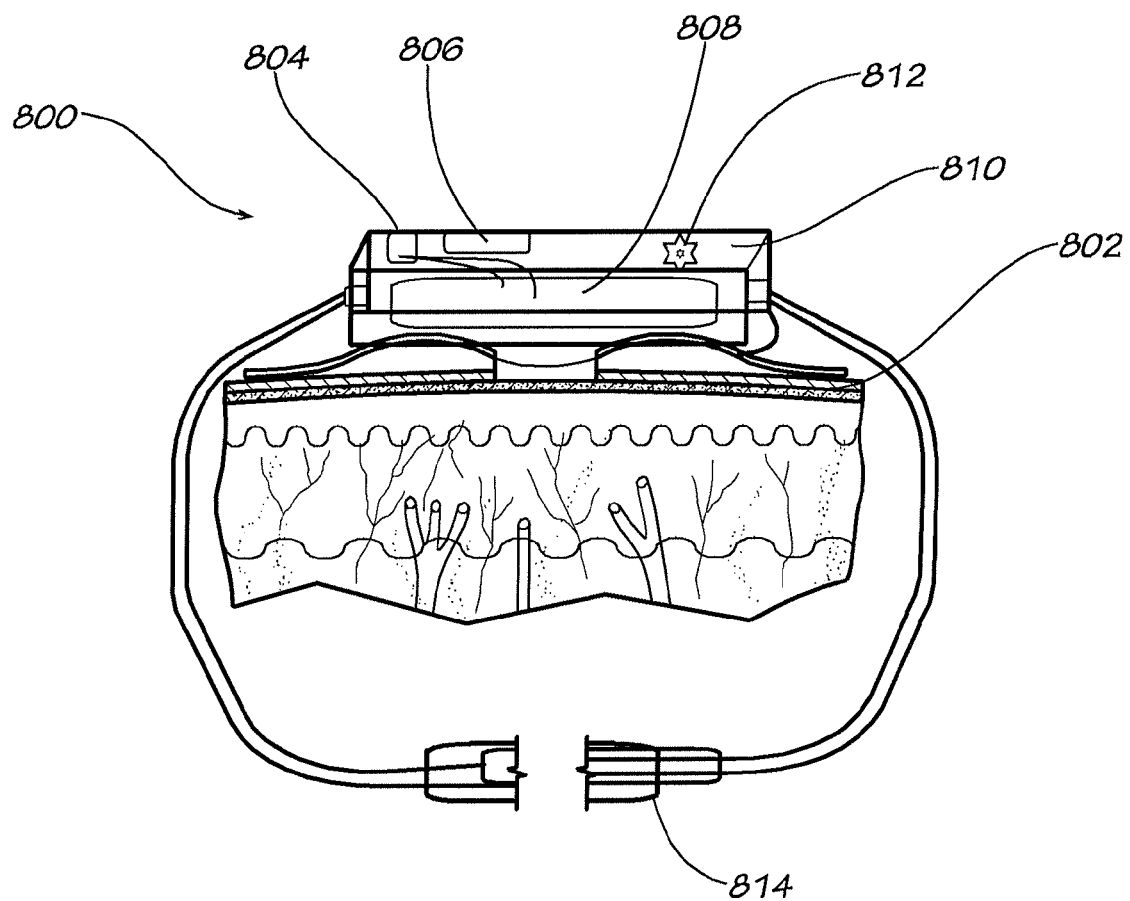
FIG. 17 shows a device for delivering an electromotive force positioned on top of a transdermal delivery device.

FIG. 17 is the diagrammatic presentation of a device 800 for imparting electromotive force (e.g., vibration, ultrasound) 800 on a transdermal delivery device 802. In this aspect, the transdermal delivery device 802 is applied on the skin followed by positioning of device 800 on the surface of the transdermal delivery device. Combining the both methods will enhance and accelerated the development of effective analgesia/anesthesia to introduce a sharp object such as injection needles, and lancets. This diagram shows on and off electrical switch 804, battery housing 806, vibration (Vibrator) device 808 inside the vibratory control box 810. It also has vibration adjuster potentiostatic switch 812 with Velcro straps 814 to hold device 800 in position on the transdermal delivery device 600.

In another aspect, a small battery-powered ultrasound transducer can be provided for producing a low-frequency (approximately 20 kHz) ultrasonic energy to the skin for 20 to 120 seconds prior to and/or after the application of the transdermal delivery device to the skin. Not wishing to be bound by theory, the ultrasound waves open small cavities in the skin by disorganizing the lipid bi-layer, creating tiny, reversible channels through which the local anesthetics, anti-microbial and other therapeutic agents are delivered to the deeper layers of the skin. The ultrasound also disrupts and breaks open the microbes at the site of injection, thus reducing the chances of infection of the site of injection and/or the microbes being carried to the deeper layers of the skin. Further, the antibiotics, and antibacterial and antiviral therapeutic agents become more effective in keeping the injection patch port of the transdermal delivery device sterile. The microscopic openings created in the skin by ultrasound are much too small to see, but large enough for molecules relevant to medicine to pass through the skin and mucous membranes.

The ultrasound transducer can be in the form of a piezoelectric transducer, which when excited by electricity, vibrates at frequencies above sound. Such a transducer can be used in place of the vibratory motors described herein or can be used in conjunction therewith. The transducer can be a piezoelectric crystal, ceramic, polymer, or composite. Typically, such transducers tend to operate at a harmonic frequency at a fixed frequency that is directly related to the thickness of the transducer (hence, for many ultrasound transducers, the frequency of the harmonic vibrations is not variable, typically). The electric circuit and control for such a transducer can take advantage of this harmonic tendency by driving the transducer at a sympathetic (matching) frequency. Thus, the circuit is designed to match the harmonics of the transducer and drive the transducer with an oscillating signal that matches the harmonic frequency of the transducer. Of course, other circuit designs can be employed, as desired, and this is merely one example. In addition, the ultrasound transducer is driven to be either off or on and the circuit needs an on/off switch of some sort and an appropriate power supply.

The devices and methods described herein can be used to treat various painful conditions of the fingers, phalanges, nails, etc, including trauma, infection, fractures, tendon tears, burns, allergic reactions, any and all painful conditions of the digits, toes and nails of the hand and leg besides relieving the pain of lancing the pulp of the digits to draw blood.

The devices and methods described herein are particularly useful in the treatment of chronic disorders, systemic diseases, and hormone replacement therapy. Such chronic and systemic diseases include, for example, diabetes, psoriasis, and eczema. In the case of diabetes, the subject is continuously monitoring blood sugar levels as well as self-administering insulin. The continuous pricking and injections can be traumatic to the subject over time. The devices described herein alleviate the pain and stress associated with this, which will ultimately ensure that the subject is diligent with monitoring their blood sugar levels and consistently administering their medication.

In another aspect, the transdermal delivery devices and methods described herein can be used for reducing or eliminating pain associated with bruises, cuts, poison ivy irritation, insect bites and stings, localized skin diseases, and allergic reactions without using the injection port.

In yet another aspect, the transdermal delivery devices and methods described herein can be used to deliver either locally or systemically any one of the substances, chemicals, hormones, or therapeutic agents mentioned above.

Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for reducing or eliminating pain associated inserting a needle into the skin of a subject comprising prior to insertion of the needle into the skin
   a. applying a transdermal delivery device to the skin of the subject, wherein the transdermal delivery device comprises at least one re-sealable injection port and at least one local anesthetic reservoir for delivering the anesthetic to the skin of a subject, wherein the local anesthetic reservoir is compartmentalized into at least two separate reservoirs, and wherein the at least one local anesthetic reservoir surrounds the at least one re-sealable injection port, and the re-sealable injection port is separated from the local anesthetic reservoir by an impermeable substrate; and
   b. applying an electromotive force to the skin of the subject, wherein the electromotive force can be applied to the skin prior to the application of the transdermal delivery device to the skin, after the application of the transdermal delivery device to the skin, or a combination thereof.

2. The method of claim 1, wherein the local anesthetic reservoir further comprises at least one re-sealable refill port for refilling the local anesthetic reservoir.

3. The method of claim 1, wherein an antiseptic agent is coated on one or both surfaces of the at least one re-sealable injection port.

4. The method of claim 1, wherein the electromotive force comprises of iontophoresis, electroosmosis, electroporation, fractional laser, a magnetic force, vibration, vibroacoustic force, a sonophoretic force, or any combination thereof.

5. The method of claim 1, wherein the electromotive force is ultrasound, wherein the ultrasound is applied to the skin prior to the application of the transdermal delivery device.

6. The method of claim 1, wherein the electromotive force is ultrasound, wherein the ultrasound is applied to the transdermal delivery device after the device has been applied to the skin.

7. The method of claim 1, wherein the electromotive force is ultrasound, wherein the ultrasound is applied to the skin prior to the application of the transdermal delivery device and ultrasound is applied to the transdermal delivery device after the device has been applied to the skin.

8. The method of claim 1, wherein the skin is located at a digit of a subject.

9. The method of claim 1, wherein the electromotive force comprises vibration, wherein the vibration is delivered by a device comprising:
  a. a ring-like vibratory element adapted to be fitted about the digit temporarily; and
  b. a controller coupled to the ring-like vibratory element for controlling operation of the ring-like vibratory element.

10. The method of claim 9, wherein the ring-like vibratory element comprises a first section and a second section hingedly coupled to the first section at first ends thereof.

11. The method of claim 10, wherein the first and second sections of the ring-like vibratory element are each generally C-shaped.

12. The method of claim 9, wherein the device further comprises first and second elastic elements for elastically securing opposite ends of the first and second sections to one another.

13. The method of claim 9, wherein the device further comprises an elastic element for elastically securing second ends of the first and second sections to one another.

14. The method of claim 9, wherein the ring-like vibratory element includes an inner elastic loop adapted to be slipped around a digit and one or more vibratory motors mounted to the outside of the inner elastic loop.

15. The method of claim 9, wherein the ring-like vibratory element comprises an ultrasonic element.

16. The method of claim 1, wherein the electromotive force comprises vibration, wherein the vibration is delivered a device comprising:
  a. a ring-like part adapted to be fitted about the digit temporarily;
  b. a pair of vibratory elements positioned on opposite sections of the ring-like part for vibrationally stimulating opposite sides of a subject's digit; and
  c. a controller coupled to the vibratory elements for controlling operation of the vibratory elements.

17. The method of claim 16, wherein the vibratory elements comprises a first section and a second section hingedly coupled to the first section at first ends thereof.

18. The method of claim 16, wherein the vibratory elements are each generally C-shaped.

19. The method of claim 1, wherein the device comprises a first side and second side, wherein the first side comprises an impermeable material surrounding the injection port, the second side comprises a permeable or semi-permeable material, wherein the impermeable material of the first side and the permeable or semi-permeable material of the second side forms the local anesthetic reservoir, and the permeable or semi-permeable material permits the diffusion of the local anesthetic from the local anesthetic reservoir.

20. The method of claim 19, wherein the periphery of the permeable or semi-permeable material on the second side is surrounded by a second impermeable material.

21. The method of claim 20, wherein an adhesive is present on the surface of the second impermeable material.

22. The method of claim 19, wherein one or more re-sealable refill ports are present on the first side of the device.

23. The method of claim 19, wherein the device comprises two or more injection ports.

* * * * *